(12) United States Patent
Cho et al.

(10) Patent No.: US 8,634,515 B2
(45) Date of Patent: Jan. 21, 2014

(54) METHOD AND APPARATUS FOR OBTAINING PANORAMIC IMAGE

(75) Inventors: Hyosung Cho, Gangwondo (KR); Sungil Choi, Gyeonggi-do (KR); Yangseo Koo, Gyeonggi-do (KR)

(73) Assignee: Vatech Co., Ltd., Gyeonggi-do (KR)

( * ) Notice: Subject to any disclaimer, the term of this patent is extended or adjusted under 35 U.S.C. 154(b) by 363 days.

(21) Appl. No.: 13/093,380

(22) Filed: Apr. 25, 2011

(65) Prior Publication Data
US 2012/0268556 A1 Oct. 25, 2012

(51) Int. Cl.
*A61B 6/14* (2006.01)

(52) U.S. Cl.
USPC .............................. 378/38; 378/27; 378/98.12

(58) Field of Classification Search
USPC .................. 378/21–27, 38–40, 62, 98.12; 382/130–132
See application file for complete search history.

(56) References Cited

U.S. PATENT DOCUMENTS

| | | | | |
|---|---|---|---|---|
| 5,784,429 A * | 7/1998 | Arai | | 378/38 |
| 6,570,953 B1 * | 5/2003 | Dobert et al. | | 378/21 |
| 7,336,763 B2 * | 2/2008 | Spartiotis et al. | | 378/40 |
| 7,545,909 B2 * | 6/2009 | Singh et al. | | 378/39 |
| 8,165,265 B2 * | 4/2012 | Niwa et al. | | 378/39 |
| 2011/0064188 A1 * | 3/2011 | Suzuki et al. | | 378/21 |

FOREIGN PATENT DOCUMENTS

WO  WO 2007/110465  10/2007

* cited by examiner

*Primary Examiner* — Thomas R Artman
(74) *Attorney, Agent, or Firm* — IP Legal Services, LLC

(57) ABSTRACT

A method of obtaining a panoramic image and an apparatus for the same are disclosed. In particular, a method of obtaining a panorama image and an apparatus for the same capable of obtaining a more clear panoramic image with reproducibility by extracting best-focused-images in case of forming images of multiple image-layer-trace images are disclosed. In accordance with the method and the device of this invention for obtaining the panoramic image, it is possible to complete the optimal image-layer-trace to be reconstructed and to obtain a clear panoramic image which vividly shows an arch of a patient by reconstructing a panoramic image for an optimal image-layer-trace most closely related to a focus-trace.

15 Claims, 12 Drawing Sheets

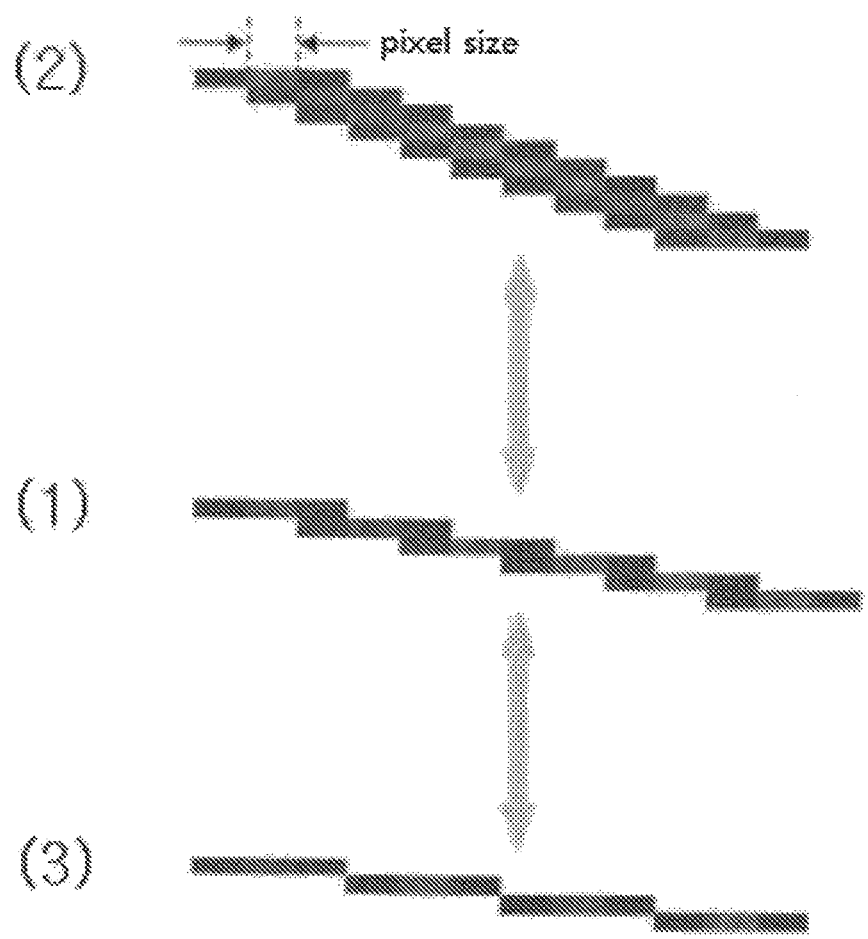

METHOD AND APPARATUS FOR OBTAINING PANORAMIC IMAGE

FIELD OF THE INVENTION

This invention relates to a method of obtaining a panoramic image and an apparatus for the same, in particular, a method of obtaining a panorama image and an apparatus for the same capable of obtaining a more clear panoramic image with reproducibility by extracting best-focused-images in case of forming images of multiple image-layer-trace images.

BACKGROUND OF THE INVENTION

In general, a panoramic image is referred wall image obtained by connecting images captured along a predetermined image-trace where the images to be formed.

FIG. 1 is a diagram showing a conventional panoramic imaging apparatus.

According to FIG. 1, the conventional panoramic image obtains a panoramic image by reconstructing images formed by rotating an X-ray source 12 and an image sensor 13 around an image-layer-trace 11 as a determined trace where regions of interest 14 of an object are located. The image-layer-trace 11 is referred to regions where focuses of the panoramic imaging apparatus are located. The panoramic imaging apparatus exposes the X-ray to all the regions of the image-layer-trace 11 and forms the panoramic image by connecting the formed images.

In the conventional panoramic image, arbitrary image-trace regions have been determined in a predetermined trace, and the conventional panoramic image layer shows an image obtained at the predetermined image-layer-trace. In other words, the pixels defined as an imaging area is positioned to the image-layer-trace in consideration of the magnification. The images are formed with a constant pixel interval, and then the images are connected by matching the pixels of the image regions to obtain the image of a target image-layer-trace.

SUMMARY OF THE INVENTION

This invention provides a method and an apparatus for completing an optimal image-layer-trace to be reconstructed by automatically analyzing an image-layer-trace most closely related to a focus-trace among multiple image-layer-traces in each region.

Further, this invention provides a method and an apparatus for obtaining a panoramic image capable of obtaining a clear panoramic image which vividly shows an arch of a patient by performing the reconstruction for an optimal image-layer-trace most closely related to a focus-trace.

Also, this invention provides a method and an apparatus for obtaining a panoramic image capable of obtaining a clear panoramic image by preventing the generation of errors in connection parts even tough using multiple image-layer-traces and composing an optimal image-layer-trace regardless of skill of operators.

This invention provides a method of obtaining a panoramic image may include steps of: obtaining panoramic images of regions of interest to be taken in an object, wherein the panoramic images are correspond to multiple image-layer-traces; dividing the multiple image-layer-traces into at least two regions and selecting an optimal image-layer-trace closely related to a focus-trace in each region: completing a final-trace by connecting the optimal image-layer-trace selected in each region and reconstructing a panoramic image corresponding to the final-trace.

In accordance with a desirable embodiment, the step of selecting the optimal image-layer-trace may be performed with a frequency analysis.

In accordance with a desirable embodiment, the region of interest may be an arch of a patent.

This invention provides a method of obtaining a panoramic image may include the steps of: 1) obtaining panoramic images of regions of interest to be taken in an object, wherein the panoramic images are correspond to multiple image-layer-traces: 2) dividing the multiple image-layer-traces into at least three regions respectively and determining at least two analysis regions: 3) selecting an optimal image-layer-trace closely related to a focus-trace by analyzing the multiple image-layer-traces in the same analysis region: 4) extracting a connecting-trace linking the optimal image-layer-traces selected in the regions: 5) completing a final-trace by connecting the optimal image-layer-trace selected in each region and the connecting-trace all together: and 6) reconstructing a panoramic image corresponding to the final-trace.

In accordance with a desirable embodiment, obtaining the panoramic images corresponding to the multiple image-layer-traces at step 1) is reconstructed to a panoramic image corresponding to the analysis region.

In accordance with a desirable embodiment, the extracting the connecting-trace at the step 4) may include finding a logarithmic function consistent with a trace linking the optimal image-layer-traces selected in the region. A base trace of an arch is determined with the logarithmic function.

In accordance with a desirable embodiment, the multiple image-layer-traces may be divided into five (5) regions at the step 2), and the analysis region is determined with a first region corresponding to left posterior teeth, a third region corresponding to anterior teeth and a fifth region corresponding to right posterior teeth.

In accordance with a desirable embodiment, the step 3) of selecting the optimal image-layer-trace most closely related to the focus-trace may be performed with a frequency analysis.

In accordance with a desirable embodiment, the region of interest may be an arch of a patent.

This invention provides a method of obtaining a panoramic image may include steps of: 1) positioning an object between an X-ray source exposing X-rays to a base image-layer-trace where regions of interest to he taken in an object and an image sensor receiving the X-rays having penetrated the base image-layer-trace exit: 2) obtaining a frame image of a first region of the base image-layer-trace by exposing the X-rays to the first region, a start portion of the base image-layer-trace: 3) obtaining frame images from a second region adjacent to the first region of the base image-layer-trace to an $n^{th}$ region, an end portion of the base image-layer-trace, as the X-ray source and the image sensor move: 4) obtaining panoramic images correspond to multiple image-layer-traces with use of the frame image of each region of the base image-layer-trace; 5) dividing the multiple image-layer-traces into at least three regions respectively and determining at least two analysis regions ; 6) selecting an optimal image-layer-trace closely related to a focus-trace by analyzing the multiple image-layer-traces in the same analysis region: 7) extracting a connecting-trace linking the optimal image-layer-trace selected in each analysis region; 8) completing a final-trace by connecting the optimal image-layer-trace selected in each analysis region and the connecting-trace all together; and 9) reconstructing a panoramic image corresponding to the final-trace, wherein, at the steps 2) and 3), X-rays penetrating each region of the base image-layer-trace are exposed to be over lapped with the X-rays having penetrated previous region of the base image-layer-trace.

In accordance with a desirable embodiment, the obtaining panoramic images correspond to multiple image-layer-traces at the step 4) may include reconstructing a base panoramic image with the frame of each region of the base image-layer-trace, reconstructing an inner panoramic image of an inner image-layer-trace by overlapping pixels of the frame images having used to reconstruct the base panoramic image by an overlapping amount larger than an overlapping image of the pixels in reconstructing the base panoramic image, and reconstructing an outer panoramic image of an outer image-layer-trace by overlapping the pixels of the frame images having used to reconstruct the base panoramic image by an over lapping amount smaller than the over lapping image of the pixels in reconstructing the base panoramic image or without overlapping the pixels.

In accordance with a desirable embodiment, the inner panoramic image of the inner image-layer-trace and the outer panoramic image of the outer image-layer-trace may be reconstructed only with the image-layer-traces in the analysis regions.

In accordance with a desirable embodiment, the extracting the connecting-trace at the step 7) may include finding a logarithmic function consistent with a trace linking the optimal, image-layer-traces selected in the region. A base trace of an arch is determined with the logarithmic function.

In accordance with a desirable embodiment, the region of interest may be an arch of a patent.

In accordance with a desirable embodiment, the multiple image-layer-traces may be divided into five (5) regions at the step 2), and the analysis region is determined with a first region corresponding to left posterior teeth, a third region corresponding to anterior teeth and a fifth region corresponding to right posterior teeth.

In accordance with a desirable embodiment, the step 3) of selecting the optimal image-layer-trace most closely related to the focus-trace may be performed with a frequency analysis.

In accordance with a desirable embodiment, the respective images of each pixel obtained by overlapping the pixels of the frame images used to forming the panoramic image at step 4) are the images obtained by varying shooting angles to the same region of the image-layer-trace.

In accordance with a desirable embodiment, the X-ray source may be controlled to expose the X-rays to the regions, respectively, and the image sensor is controlled to receive the X-rays interworking with the X-ray source.

This invention provides an apparatus for obtaining a panoramic image may include an X-ray source exposing X-rays to multiple image-layer-traces where regions of interest of an object exit: an image sensor receiving the X-rays having penetrated the multiple image-layer-traces and obtaining images of the image-layer-traces: and an image processing device receiving the image obtained by the image sensor and reconstructing panoramic images of the image-layer-traces, wherein the image processing device includes: a trace selecting unit for dividing the multiple image-layer-traces into at least two regions and selecting an optimal image-layer-trace closely related to a focus-trace in each region: a final-trace completing unit for completing a final-trace by connecting the optimal image-layer-traces selected in the regions; and an image reconstructing unit for reconstructing a panoramic image corresponding to the final-trace.

This invention may provide an apparatus for obtaining a panoramic image, including: an X-ray source exposing X-rays to multiple image-layer-traces where regions of interest of an object exit; an image sensor receiving the X-rays having penetrated the multiple image-layer-traces and obtaining images of the image-layer-traces: and an image processing device receiving the image obtained by the image sensor and reconstructing panoramic images of the image-layer-traces, wherein the image processing device includes: a region determining unit for dividing the multiple image-layer-traces into at least three regions and determining at least two analysis regions: a trace selecting unit for analyzing the multiple image-layer-traces in the analysis regions to select an optimal image-layer-trace closely related to a focus-trace in each region; a connecting-trace extracting unit for extracting a connecting-trace linking the optimal image-layer-traces selected in the regions; a final-trace completing unit for completing a final -trace by connecting the optimal image-layer-trace selected in each region and the connecting-trace all together; and an image reconstructing unit for reconstructing a panoramic image corresponding to the final-trace.

An apparatus for obtaining a panoramic image may include an X-ray source exposing X-rays to a base image-layer-trace where regions of interest of an object exit; a controlling module for exposing the X-rays to all regions of the base image-layer-trace and controlling exposure of the X-rays to overlap the X-rays penetrating each region of the base image-layer-trace with the X-rays having penetrated previous region of the base image-layer-trace: and an image processing device receiving the image obtained by the image sensor and reconstructing a panoramic image of the image-layer-trace, wherein the image processing device includes: a first image reconstructing unit reconstructing panoramic image layers of multiple image-layer-traces by reconstructing a base panoramic image with the frame of each region of the base image-layer-trace, reconstructing an inner panoramic image of an inner image-layer-trace by overlapping pixels of the frame images having used to reconstruct the base panoramic image by an overlapping amount larger than an overlapping image of the pixels in reconstructing the base panoramic image, and reconstructing an outer panoramic image of an outer image-layer-trace by overlapping the pixels of the frame images having used to reconstruct the base panoramic image by an overlapping amount smaller than the overlapping image of the pixels in reconstructing the base panoramic image or without overlapping the pixels: a region determining unit for dividing the multiple image-layer-traces into at least three regions and determining at least two analysis regions: a trace selecting unit for analyzing the multiple image-layer-traces in the analysis regions to select an optimal image-layer-trace closely related to a focus-trace in each region; a connecting-trace extracting unit for extracting a connecting-trace linking the optimal image-layer-traces selected in the regions: a final-trace completing unit for completing a final-trace by connecting the optimal image-layer-trace selected in each region and the connecting-trace all together: and a second image reconstructing unit for reconstructing a panoramic image corresponding to the final-trace.

BRIEF DESCRIPTION OF THE DRAWINGS

FIG. 17 is a diagram showing a method of reconstructing various image layers by using obtained frame image.

DETAILED DESCRIPTION

Terms for illustrating this invention are selected with general ones used widely as possible, however some terms are arbitrarily selected by the applicant for certain cases. In such cases, the terms should be interpreted not by to the letter but by considering its meaning used in this detailed explanation of this invention.

Hereinafter, embodiments of the present invention are explained in detail with the reference to the attached drawings.

However, this invention is not limited to the embodiments explained herein but may be configured in other forms.

Figure 1:
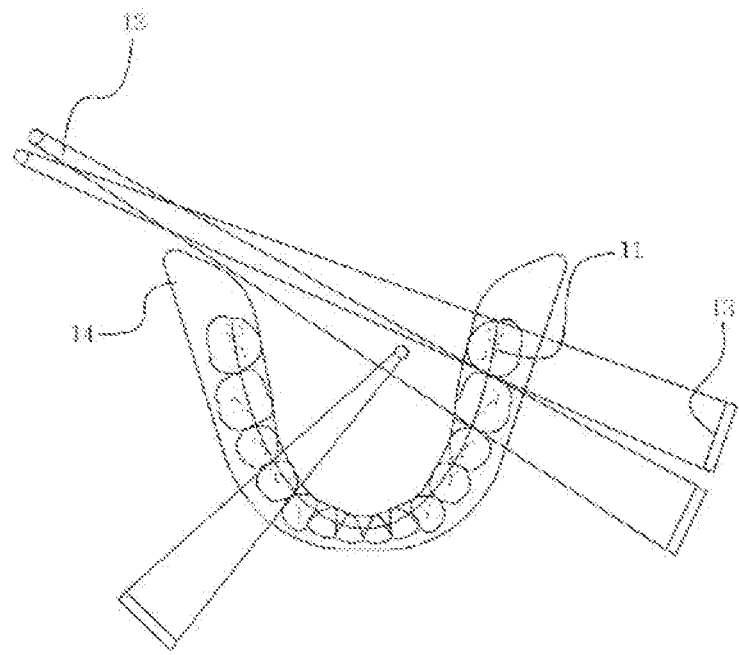
FIG. 1 is a diagram showing a conventional panoramic imaging apparatus.
Figure 2:
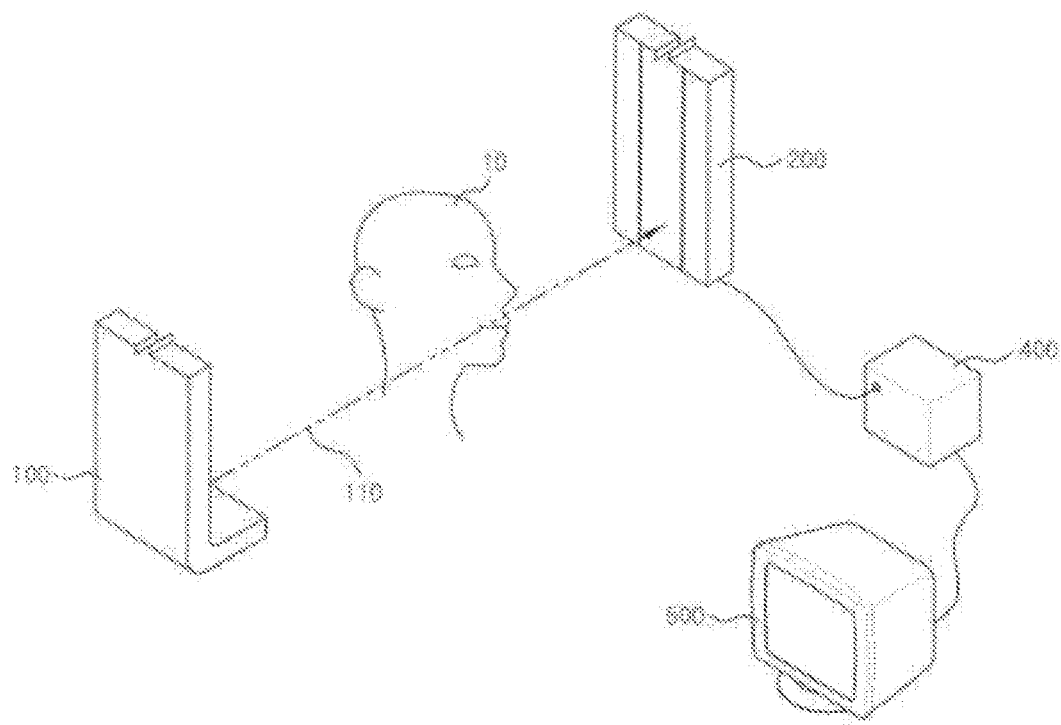
FIG. 2 shows a panoramic imaging apparatus for performing a method of obtaining a panoramic image in accordance with a first embodiment of this invention.

FIG. 1 is a diagram showing a conventional panoramic imaging apparatus. and FIG. 2 shows a panoramic imaging apparatus for performing a method of obtaining a panoramic image in accordance with a first embodiment of this invention.

Referring to FIG. 2, the panoramic imaging apparatus for performing the method of obtaining a panoramic image in accordance with a first embodiment of this invention may include an X-ray source 100, an image sensor 200, an image processing device 400 and a displaying device.

The X-ray source 100 may expose the X-rays with rotating around an object 10 along a predetermined trace. At this time, the X-ray source 100 may expose the X-rays to the multiple image-layer-traces (refer FIG. 4) where regions of interest of the object exit. Here, the regions of interest are referred to intended portions to be taken in the object 10.

The image sensor 200 may have a constant area and move in conjunction with the X-ray source with the object 10 therebetween to forms images of the multiple image-layer-traces by receiving the X-rays.

The image processing device 400 may reconstruct the images corresponding to the image-layer-traces by receiving the images obtained at the huge sensor 200 and a panoramic image for a final-trace.

The displaying device 500 may display the panoramic image corresponding to he final-trace to a user, reconstructed at the image processing device 400.

Figure 3:
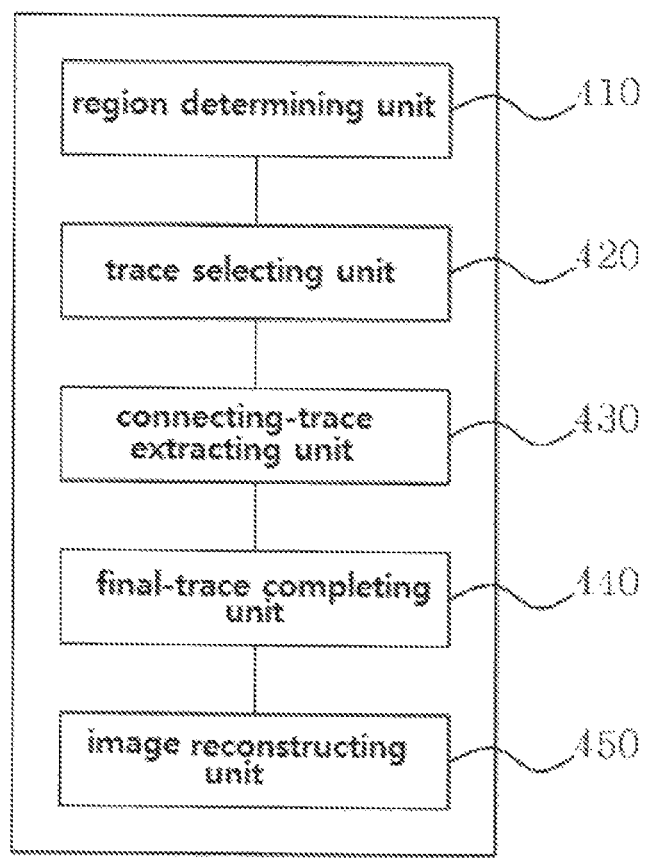
FIG. 3 shows a diagram illustrating an image processing device equipped in the panoramic imaging device in accordance with the first embodiment of this invention.

Referring to FIG. 3. the image processing device 400 may include a region determining unit 410, a trace selecting unit 420, a connecting-trace extracting unit 430, a final-trace completing unit 440 and an image reconstructing unit 450.

The region determining unit 410 may divide the multiple image-layer-traces into at least three regions and determine at least two analysis regions.

The trace selecting unit 420 may analyze the multiple image-layer-traces in the analysis regions to select an optimal image-layer-trace closely related to a focus-trace in each region. The trace selecting unit 420 may select the optimal image-layer-trace of each region with various methods. In an embodiment of this invention, the optimal image-layer-trace of each region may be selected with a frequency analysis. More detailed explanation will be mentioned later referring to FIG. 6.

The connecting-trace extracting unit 430 may extract connecting-trace linking the optimal image-layer-traces selected in the region. The connecting-trace extracting unit 430 may extract the connecting-trace with various methods. In an embodiment of this invention, the connecting-trace extracting unit extracts the connecting-trace by finding logarithmic function consistent with a linking the optimal image-layer-trace selected in each region.

The final-trace completing unit 440 may complete the final-trace by connecting the optimal image-layer-trace selected in each region and the connecting-trace all together.

The image reconstructing unit 450 may reconstruct the panoramic image corresponding to the final-trace.

FIGS. 4 to 8 are diagrams showing a method of obtaining the panoramic image in accordance with a first embodiment of this invention, where an arch of a patient, i.e., object is taken.

Hereinafter, the method of obtaining a panoramic image is explained referring to FIGS. 4 to 8. and the explanations on elements identical to those of FIG. 2 will be omitted.

Figure 4:
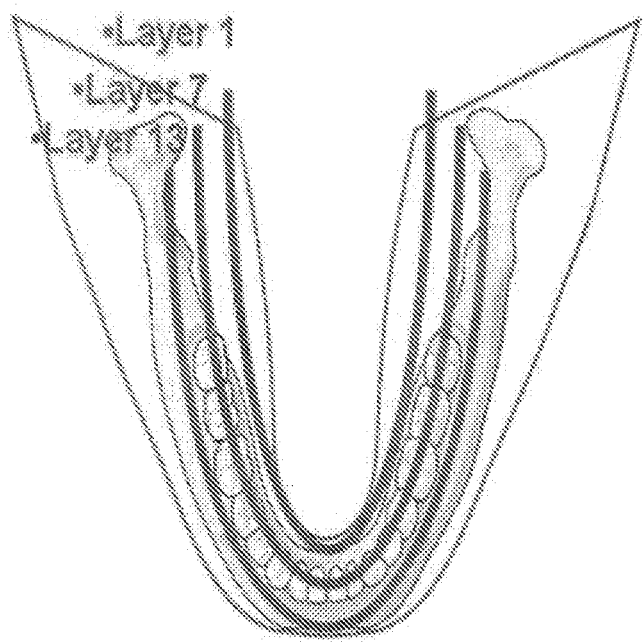
FIGS. 4 to 8 are diagrams showing a method of obtaining the panoramic image in accordance with a first embodiment of this invention.

Referring to FIG. 4. panoramic images of regions of interest in an object may be taken. At this time, the panoramic images corresponding to multiple image-layer-traces may be taken (S110). Here, the regions of interest may be referred to intended portions to be taken in the object and may mean an arch of a patent in the first embodiment of this invention.

The method of obtaining panoramic images corresponding to the multiple image-layer-traces may be various. For example, the panoramic images corresponding to the multiple image-layer-traces may be obtained at a time with one time of panoramic image capturing.

At this time, a method of reconstructing panoramic images for all regions of the image-layer-traces by using the images obtained by the panoramic image capturing may be adopted as the method of obtaining panoramic images corresponding to the multiple image-layer-traces.

Further, the panoramic images may be reconstructed with images corresponding to some regions of the multiple image-layer-traces. In other words. the panoramic images may be reconstructed for the image-layer-traces in analysis regions to be explained later. If this method is used, it is not required to reconstruct the panoramic image for all the regions of the multiple image-layer-traces. Thus, time may be reduced.

The number of image-layers-traces may he determined among lots of numbers. As shown in FIG. 4, three image-layer-traces. i.e., one, seven and thirteen image-layer-trances among multiple image-layer-traces may be arbitrarily selected.

Next, the multiple image-layer-traces are divided into at least three regions, and at least two analysis regions may be determined (S120).

Figure 5:
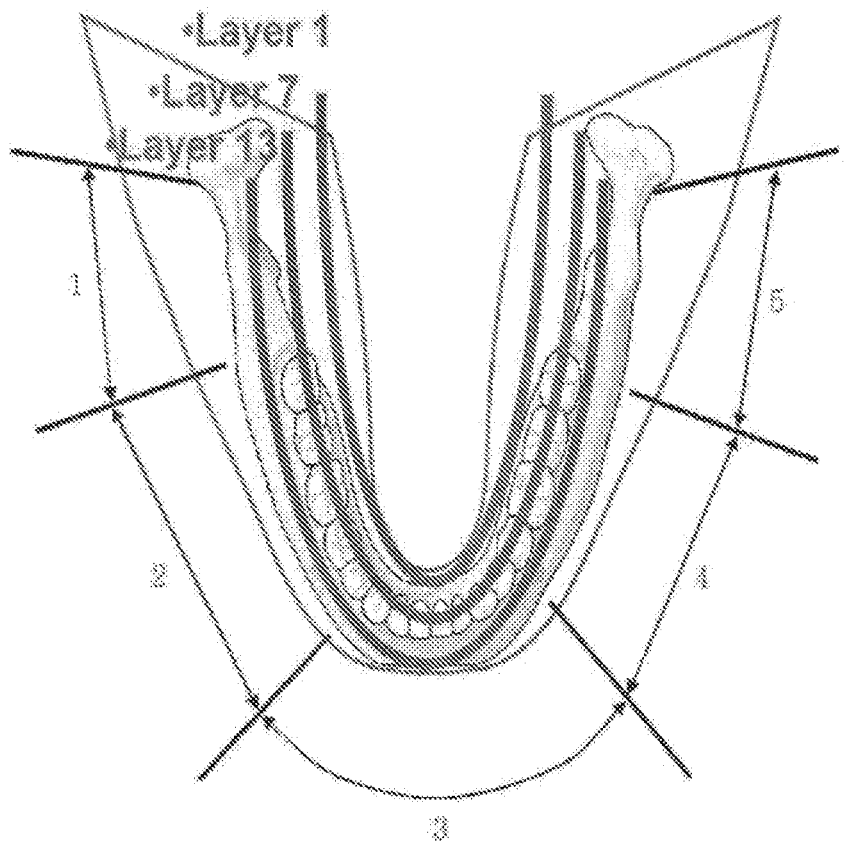

Referring to FIG. 5, the multiple image-layer-traces may be divided into five (5) regions, and three regions (a first region, a third region and a fifth region) are determined as the analysis regions.

At this time, the first region corresponds to left posterior teeth, the third region corresponds to anterior teeth, and the fifth region corresponds to right posterior teeth. A second and a forth regions are non-analysis regions.

Next, the multiple image-layer-traces in the same analysis region may be analyzed to select an optimal image-layer-trace most closely related to a focus-trace in each region (S130). The focus-trace means is a trace determined when a magnification of image is matched to meet a position of the object. The focus-trace means an image region shows the shape of the object most clearly. The focus-trace is a trace having exact geometrical information and also is the trace requisitely formed during the process of capturing the panoramic image.

At this time, the method of selecting the optimal image-layer-trace may be various. In the first embodiment of this invention, the optimal image-layer-trace is selected in each region by a frequency analysis.

Figure 6:
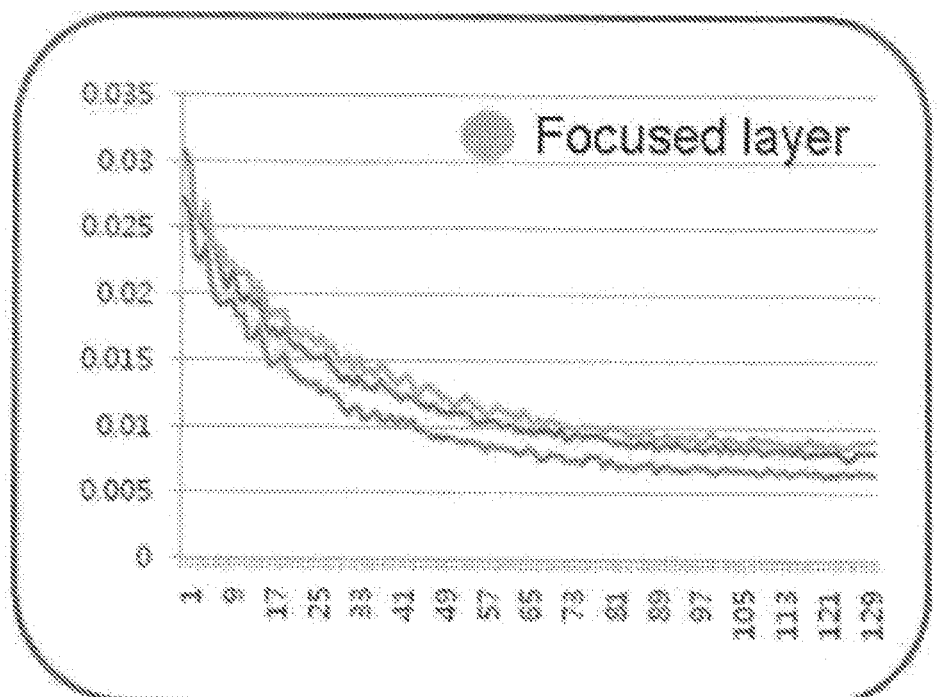

Referring to FIG. 6. spatial components of images can be analyzed by reconstructing the images of the analysis regions and performing the Fourier Transformation on the reconstructed images. The frequency component in the image represents the contrast distribution depending spatial position in each image. A clear image has high frequency values in a certain high frequency band. According to characteristics of panoramic image, the clearest image can be obtained at a well focused section. Thus, the highest frequency section in each region is selected as the optimal image-layer-trace.

Next, a connecting-trace linking the optimal image-layer-trace selected in each region is extracted (S140). The connecting-trace may be an extracted-image-layer-trace corresponding to the non-analysis region and may be extracted by finding a logarithmic function consistent with a trace linking the optimal image-layer-trace selected in each region.

In succession, a final-trace is completed by connecting the optimal image-layer-trace selected in each region and the connecting-trace all together (S150).

Figure 7:
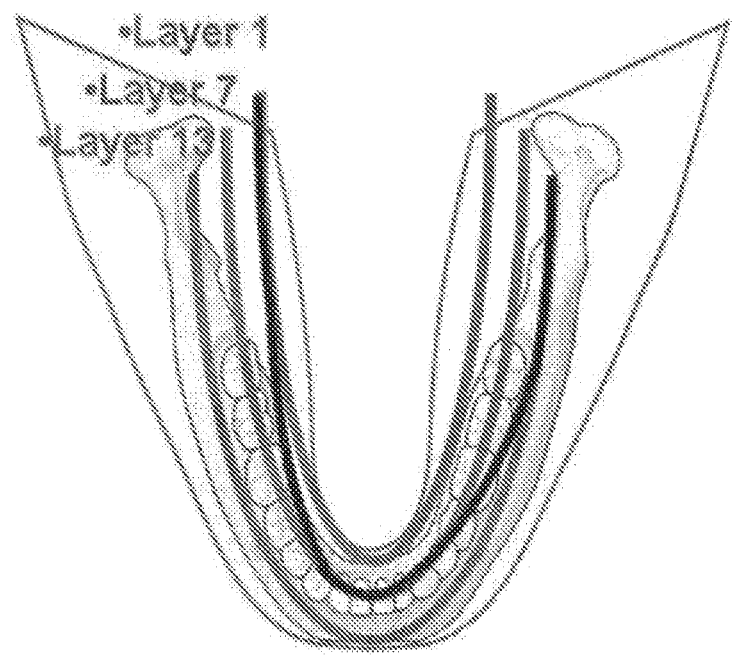

Referring to FIG. 7, the final-trace completed by connecting the optimal image-layer-trace selected in each region and the connecting-trace all together, is shown. Here, as the optimal image-layer-traces, number one image-layer-trace is selected as the result of the frequency analysis (S130) in the region 1, number seven image-layer-trace in the region 3, and number thirteen image-layer-trace is selected as the result of the frequency analysis in the region 5. Further, the connecting-trace has been extracted by the extracting method (S140) explained above.

Finally, a panoramic image corresponding to the final-trace is reconstructed (S160).

In other words, a panoramic image is reconstructed in series to the final-trace.

Figure 8:
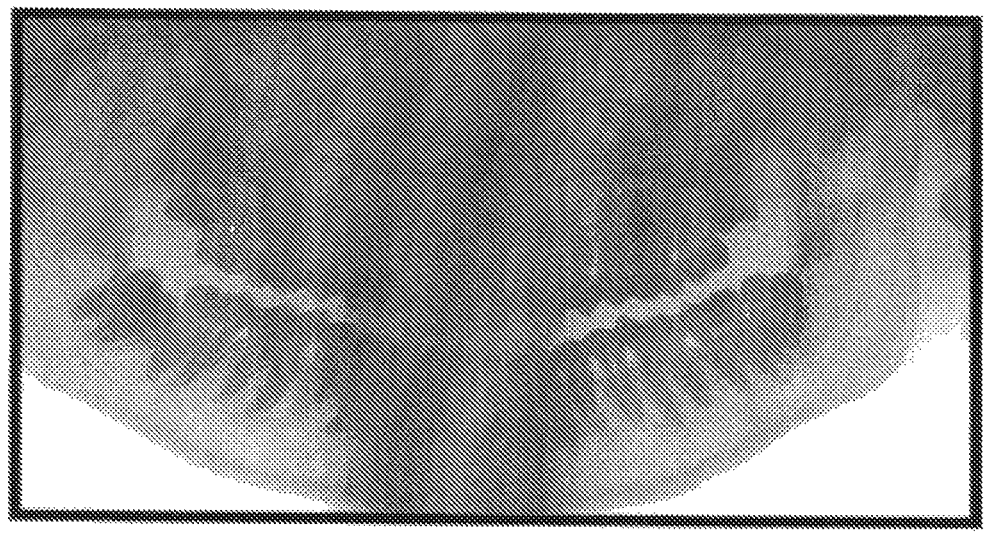

Referring to FIG. 8, the panoramic image of the arch of the patient is very clear. That is, a vivid image can be obtained since all the regions of the panoramic image are well-focused.

As explained above, in the method and the apparatus for obtaining the panoramic image in accordance with the first embodiment of this invention, the panoramic image is reconstructed to the final-trace complete by connecting the optimal image-layer-trace selected in each region and the connecting-trace all together. Thus, it is able to prevent the generation of errors caused by cutting and connecting the images in the conventional art as well as to obtain a clear panoramic image having high image quality.

Figure 9:
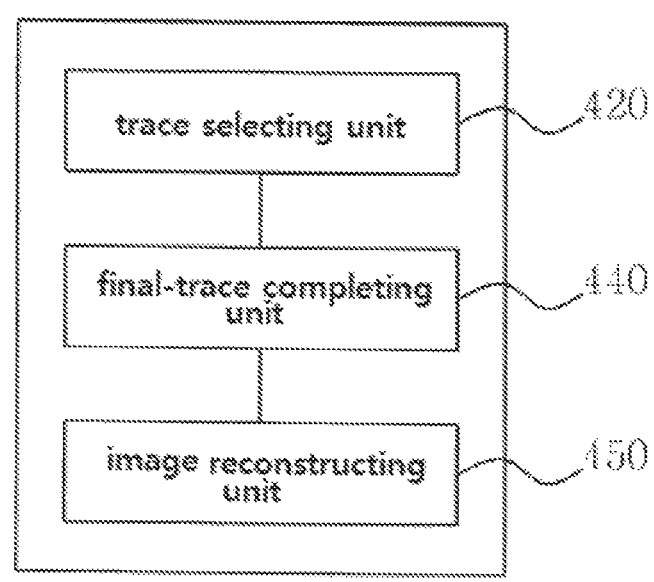
FIG. 9 shows a diagram illustrating an image processing device equipped in a panoramic imaging device in accordance with a second embodiment of this invention.

FIG. 9 shows a diagram illustrating an image processing device equipped in a panoramic imaging device in accordance with a second embodiment of this invention. The configuration of the panoramic imaging device in accordance with the second embodiment of this invention is identical to that of the panoramic imaging device in accordance with the first embodiment of this invention except the image processing device 400.

Referring to FIG. 9. the image processing device 400 may include a trace selecting unit 420, a final-trace completing unit 440 and an image reconstructing unit 350.

The trace selecting unit 420 may divide the multiple image-layer-traces into at least two regions and select an optimal image-layer-trace closely related to a focus-trace in each region.

The trace selecting unit 420 may select the optimal image-layer-trace of each region with various methods. In an embodiment of this invention, the optimal image-layer-trace of each region may be selected with a frequency analysis. More detailed explanation can be referred to the explanations mentioned above referring to FIG. 6.

The final-trace completing unit 440 may complete the final-trace by connecting the optimal image-layer-trace selected in each region and the connecting-trace all together.

The image reconstructing unit 450 may reconstruct the panoramic image corresponding to the final-trace.

Figure 10:
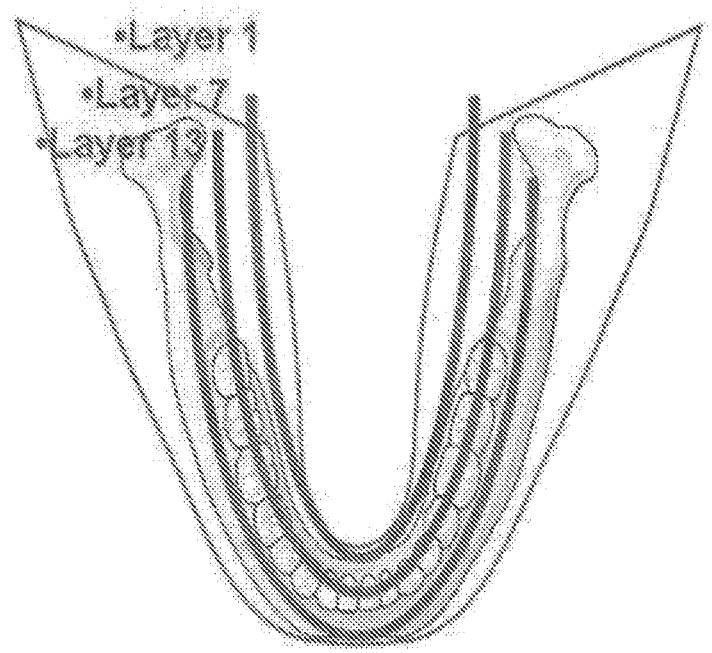
FIGS. 10 and 11 are diagrams showing a method of obtaining a panoramic image in accordance with the second embodiment of this invention.
Figure 11:
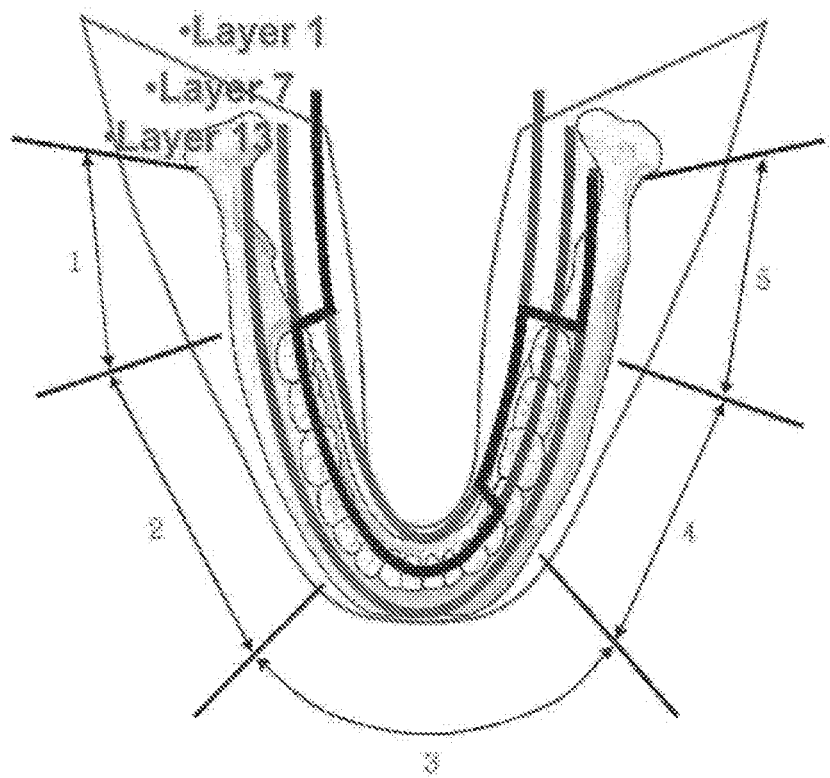

FIGS. 10 and 11 are diagrams showing a method of obtaining the panoramic image in accordance with a second embodiment of this invention, where an arch of a patient, i.e., object is taken.

Hereinafter, the method of obtaining a panoramic image is explained referring to FIGS. 10 and 11.

Referring to FIG. 10, panoramic images of regions of interest in an object, may be taken. At this time, the panoramic images corresponding to multiple image-layer-traces may be taken (S210).

The method of obtaining panoramic images corresponding to the multiple image-layer-traces may be various. For example, the panoramic images corresponding to the multiple image-layer-traces may be obtained at a time with one time of panoramic image capturing.

Next, the multiple image-layer-traces are divided into at least three regions, and a optimal image-layer-trace closely related to a focus-trace in each region is selected (S220).

Referring to FIG. 11, the multiple image-layer-traces may be divided into five (5) regions. At this time, the first region corresponds to left posterior teeth, the third region corresponds to anterior teeth, and the fifth region corresponds to right posterior teeth.

There are various ways of analyzing the multiple image-layer-traces and selecting the optimal image-layer-trace of each region. In this second embodiment the optimal image-layer-trace of each region may be selected with a frequency analysis.

In succession, a final-trace is completed by connecting the optimal image-layer-trace selected in each region (S230).

Referring again to FIG. 11, the final-trace completed by connecting the optimal image-layer-trace selected in each region, is shown. Here as the optimal number one image-layer-trace is selected as the result of the frequency analysis (S220) in the region 1, number seven image-layer-trace in the regions 2 and 3, number one image-layer-trace in region 4 and number thirteen image-layer-trace is selected as the result of the frequency analysis in the region 5.

Finally, a panoramic image corresponding to the final-trace is reconstructed (S240).

In other words, a panoramic image is reconstructed in series to the final-trace.

As explained above, in the method and the apparatus for obtaining the panoramic image in accordance with the second embodiment of this invention, the panoramic image is reconstructed to the final-trace completed by connecting the optimal image-layer-trace selected in each region. Thus, it is able to prevent the generation of errors caused by cutting and connecting the images in the conventional art as well as to obtain a clear panoramic image having high image quality.

The method and the apparatus of the second embodiment are identical to those of the first embodiment, except the configuration explained above.

Figure 12:
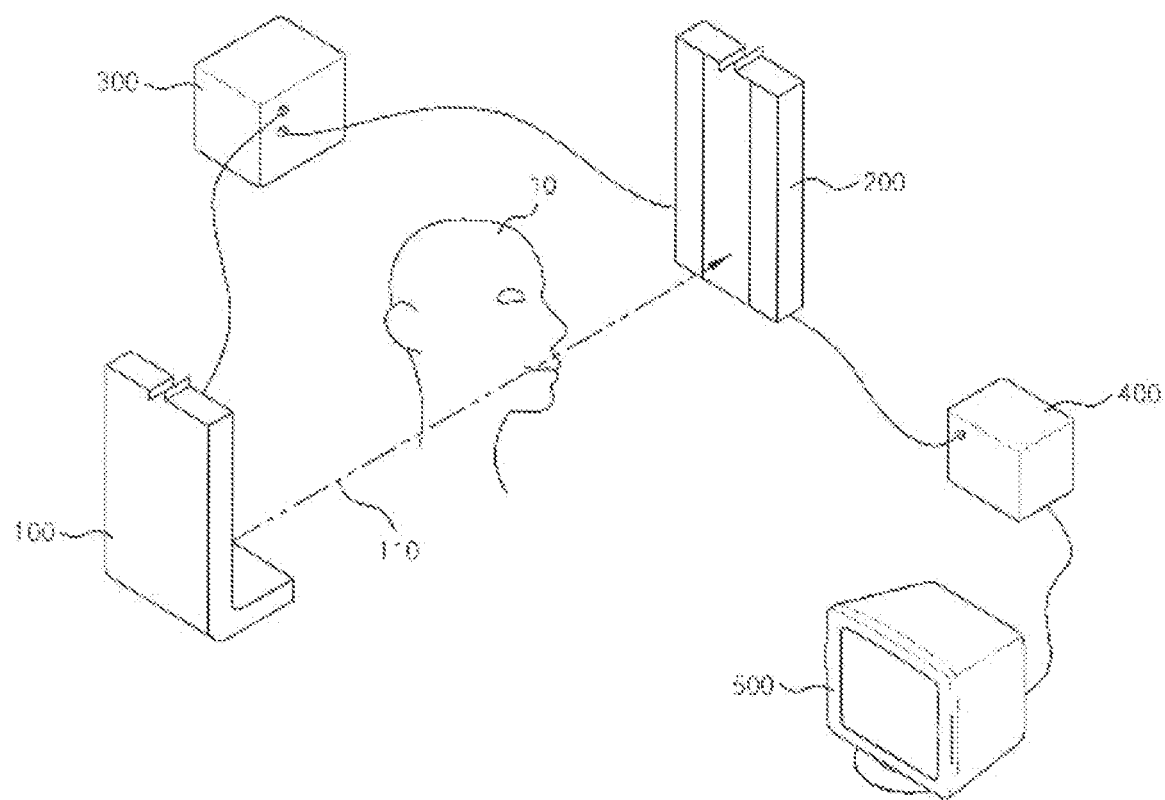
FIG. 12 shows a panoramic imaging apparatus for performing a method of obtaining a panoramic image in accordance with a third embodiment of this invention.
Figure 13:
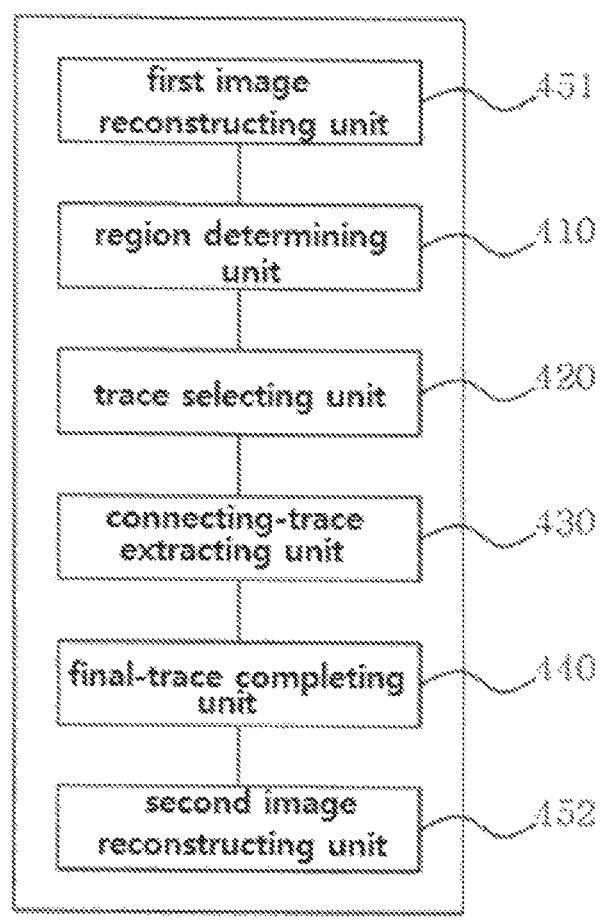
FIG. 13 shows a diagram illustrating an image processing device equipped in the panoramic imaging device in accordance with the third embodiment of this invention.

FIG. 12 shows a panoramic imaging apparatus for performing a method of obtaining a panoramic image in accordance with a third embodiment of this invention, and FIG. 13 shows a diagram illustrating an image processing device, equipped in the panoramic imaging device in accordance with the third embodiment of this invention.

Referring to FIG. 12, the panoramic imaging apparatus for performing the method of obtaining a panoramic image in accordance with a third embodiment of this invention may include an X-ray source 100, an image sensor 200, a controlling module 300, an image processing device 400 and a displaying device.

An X-ray tube (not shown) generating the X-ray is equipped within the X-ray source 100, and the X-ray source expose the X-ray 110 to an object 10 through a slit (not shown).

The X-ray source 100 may expose the X-rays intermittently with rotating around the object 10 along a predetermined trace. At this time, the X-ray source 100 may expose the X-rays to the multiple image-layer-traces (refer the reference numeral 120 of FIG. 10) where regions of interest of the object exit. Here, the regions of interest are referred to intended port ions to be taken in the object 10.

The image sensor 200 may have a constant area and move in conjunction with the X-ray source 10 with the object 10 therebetween to forms images of the regions of interest of the object located on the multiple image-layer-traces by receiving the X-rays.

Further, the image sensor 200 may obtain frame images which are unit images formed by the X-ray 110 exposed on each region.

In other words, the image sensor 200 may have a size covering only a part of the object 10 not to obtain the images of all the regions of interest at one time exposure of the X-ray and may be a small area sensor smaller than a large sensor (cephalometric-sensor) which takes the image at a time by covering all the regions of the object.

That is, the image sensor 200 obtains images of the frame unit by the X-rays exposed intermittently different from to the conventional time-delay-integration (TTI) for a continuous scan and capturing.

The image sensor 200 may be a CCD sensor or a CMOS sensor. However, the image sensor 200 may be configured with any sensor capable of receiving the X-rays.

Figure 14:
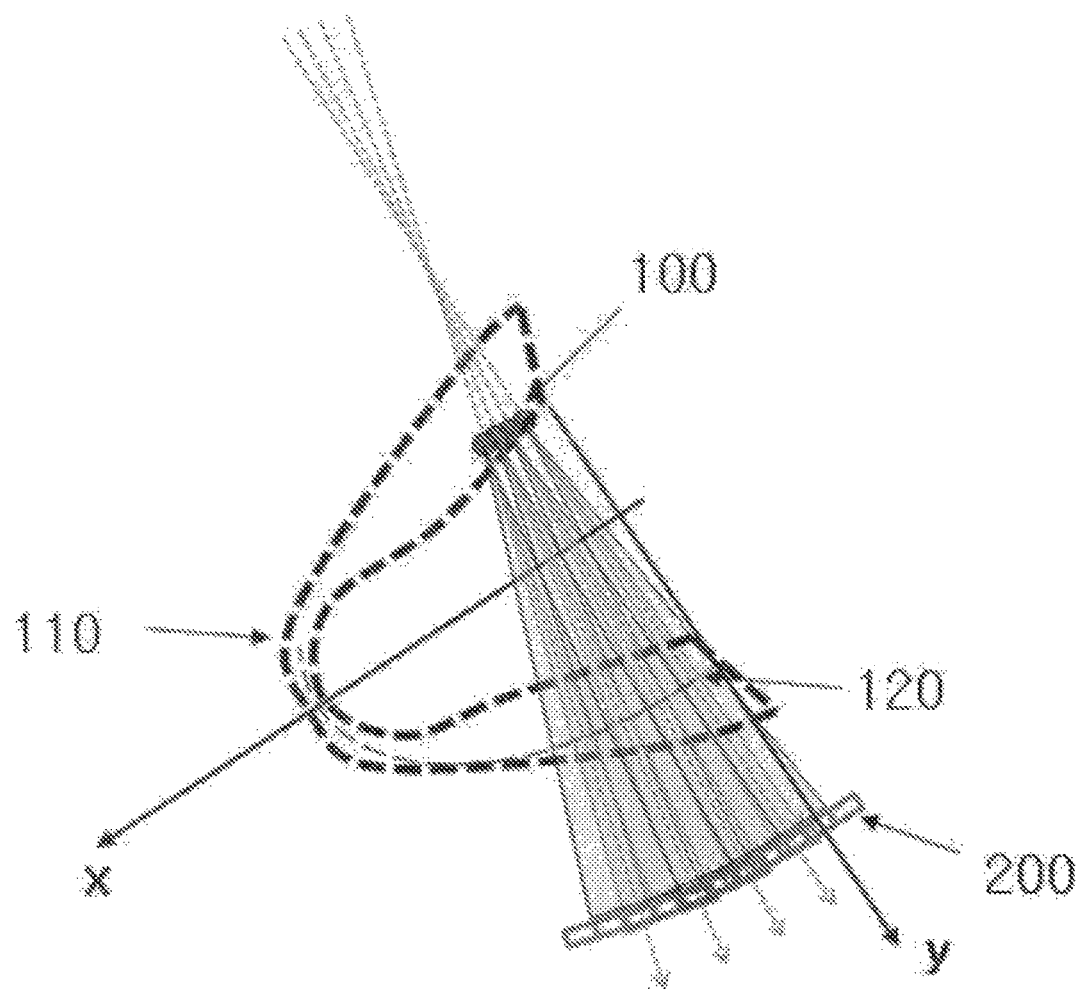
FIG. 14 is a diagram showing a method of obtaining the panoramic image in accordance with the third embodiment of this invention.
Figure 15:
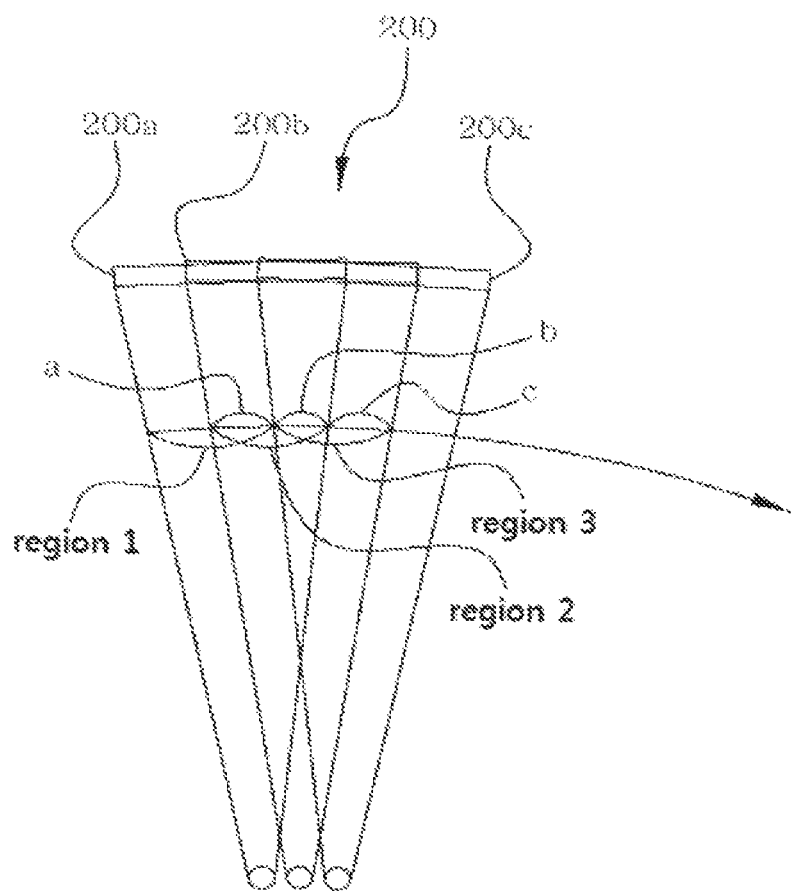
FIG. 15 is a diagram showing an overlap of X-rays being exposed to each region of a base image-layer in accordance with the third embodiment of this invention.

The movement of the X-ray source and the image sensor 200 may be explained in detail referring to FIGS. 14 and 15.

The controlling module 300 may control time of exposing the X-rays 110 by the X-ray source and time of receiving the X-rays 110 by the image sensor 200.

Further, the controlling module 300 may control of exposing the X-rays to all regions of the base image-layer-trace 120 and controlling exposure of the X-rays to overlap the X-rays penetrating each region of the base image-layer-trace 120 with the X-rays having penetrated previous region of the base image-layer-trace 120.

In other words, the controlling module 300 may control an exposure position or time when the X-ray source 100 exposes the X-rays 110 to the object 10 while the X-ray source moves.

In addition, the controlling module 300 may control the X-ray source 100 to expose the X-ray in each region and the image sensor 200 to receive the X-ray in conjunction with the X-ray source 100.

That is, the image sensor 200 may move in conjunct ion with the X-ray source 100 and per form a receiving operation to the intermittent exposing time of the X-ray for obtaining the image corresponding to the base image-layer-trace.

The image processing device 400 may receive the frame images obtained at the image sensor 200 and reconstruct the panoramic image from the image of the base image-layer-traces.

The displaying device 500 may display the panoramic image corresponding to the base image-layer-trace to a user, reconstructed at the image processing device 400.

Referring to FIG. 13, the image processing device 400 may include a first image reconstructing unit 451, a region determining unit 410, a trace select in unit 420, a connecting-trace extracting unit 430, a final-trace completing unit 440 and a second image reconstructing unit 452.

The first image reconstructing unit 451 may reconstruct a base panoramic image with the frame of each region of the base image-layer-trace, reconstructing an inner panoramic image of an inner image-layer-trace by overlapping pixels of the frame images having used to reconstruct the base panoramic image by an overlapping amount larger than an overlapping image of the pixels in reconstructing the base panoramic image, and reconstructing an outer panoramic image of an outer image-layer-trace by overlapping the pixels of the frame images having used to reconstruct the base panoramic image by an overlapping amount smaller than the overlapping image of the pixels in reconstructing the base panoramic image or without overlapping the pixels.

The region determining unit 410 may divide the multiple image-layer-traces into at least three regions and determine at least two analysis regions.

The trace selecting unit 420 may analyzing the multiple image-layer-traces in the analysis regions to select an optimal image-layer-trace closely related to a focus-trace in each region. The trace selecting unit 420 may select the optimal image-layer-trace of each region with various methods. In an embodiment of this invention, the optimal image-layer-trace of each region may be selected with a frequency analysis. More detailed explanation can be referred to the explanations mentioned above referring to FIG. 6.

The connecting-trace extracting unit 430 may extract a connecting-trace linking the optimal image-layer-trace selected in each region. The connecting-trace extracting unit 430 may extract the connecting-trace with various methods. In an embodiment of this invention, the connecting-trace extracting unit extracts the connecting-trace by finding a logarithmic function consistent with a linking the optimal image-layer-trace selected in each region.

The final-trace completing unit 440 may complete the final-trace by connecting the optimal image-layer-trace selected in each region and the connecting-trace all together.

The second image reconstructing unit 452 may reconstruct the panoramic image corresponding to the final-trace.

Figure 16:
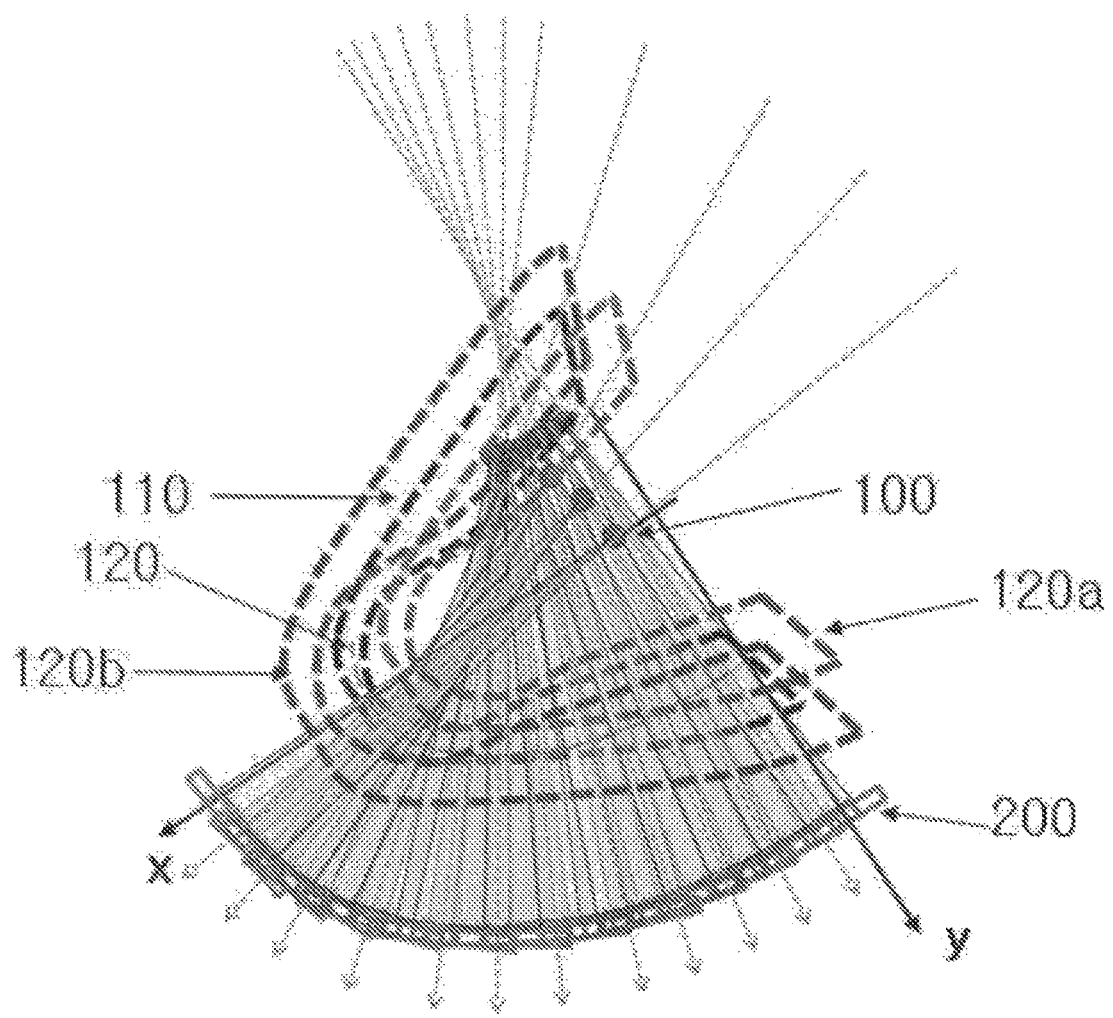
FIG. 16 is a diagram showing a method of obtaining a panoramic image in accordance with a third embodiment of this invention.

FIG. 14 is a diagram showing a method of obtaining the panoramic image in accordance with the third embodiment of this invention. FIG. 15 is a diagram showing an overlap of X-rays being exposed to each region of a base image-layer in accordance with the third embodiment of this invention. FIG. 16 is a diagram showing a method of obtaining a panoramic image in accordance with a third embodiment of this invention and FIG. 17 is a diagram showing a method of reconstructing various image layers by using obtained frame image.

Hereinafter, the method of obtaining a panoramic image is explained referring to FIGS. 14 to 17, and the explanations on elements identical to those of FIG. 12 will be omitted.

Referring to the figures, the method of obtaining a panoramic image in accordance with a third embodiment of this invention, first, the object 10 is positioned between the X-ray source 100 exposing the X-rays to the base image-layer-trace 120 where regions of interest to be taken in the object and the image sensor 200 receiving the X-rays haying penetrated the base image-lager-trace (S310).

Next, a frame image of a first region of the base image-layer-trace is obtained by exposing the X-rays to the first region, a start portion of the base image-layer-trace (S320).

In a succession, frame images from a second region adjacent to the first region of the base image-layer-trace 120 to an $n^{th}$ region, an end portion of the base image-layer-trace, as the X-ray source and the image sensor move.

At this time, the controlling module 300 may control the exposure of the X-rays by overlapping X-rays penetrating each region of the base image-layer-trace with the X-rays having penetrated previous region of the base image-layer-trace.

As shown in FIGS. 14 and 15, the X-rays from the X-ray source 100 are exposed to each region of the image-layer-trace 120, and the X-rays penetrating each region of the base image-layer-trace are overlapped with the X-rays having penetrated previous region of the base image-layer-trace. That is, the number of images obtained au the image sensor 200 may be increased by overlapping the X-rays exposed to each region of the image-layer-trace overlapped with each other.

For an example, if it assumed that the image sensor 200 is composed of three pixels, the X-rays exposed to each region of a first region, a second region and a third region of the image-layer-trace are received at the image sensor 200, respectively. At this time, an image corresponding to a region (a) of the image-layer-trace 120 is obtained repeatedly at the second pixel of the image sensor 200a and at the first pixel of the image sensor 200b, another image corresponding to a region (b) is obtained repeatedly at the third pixel of the image sensor 200a, at the second pixel of the image sensor 200b and at first pixel of the image sensor 200c. Therefore, countless number of images can be obtained for all the regions of the base image-layer-trace 120.

Here, the images of each pixel obtained by overlapping the images of the region (a), (b) or (c) of the image-layer-trace 120 are the images obtained by varying shooting angles to the same region of the image-layer-trace. Thus, more clear high resolution panoramic image can be obtained by reconstructing the frame images.

As shown in FIGS. 15 and 16, the frame images from the second region adjacent to the first region of the base image-layer-trace 120 to the $n^{th}$ region, the end portion of the base image-layer-trace can be obtained, as the X-ray source and the image sensor move.

Next, the panoramic images corresponding to multiple image-layer-traces may be taken (S210).

First, a base panoramic is reconstructed with the frame image of each region of the base image-layer-trace 120.

Referring to FIG. 17, a method of reconstructing panoramic images of multiple image-layer-traces with the obtained frame images (S340).

First, as shown in drawing (1), the image processing device 400 may reconstruct the panoramic image. That is, a base panoramic image of the base image-layer-trace may be reconstructed by over lapping the pixel of the frame images obtained at the regions respectively. At this time, one or more pixels may be overlapped each other.

As shown in drawing (2), the image processing device 400 may reconstruct the inner panoramic image of the inner image-layer-trace located inside of the base image-layer-trace 120. That is, the inner panoramic image of the inner image-layer-trace (refer 120a of FIG. 16) inside of the base image-layer-trace may be obtained by overlapping the pixels of the frame images having used to reconstruct the base panoramic image by an overlapping amount larger than an overlapping image of the pixels in reconstructing the base panoramic image.

Further, as shown in drawing (3), the image processing device 400 may reconstruct the outer panoramic image of the outer image-layer-trace located outside of the base image-layer-trace 120. That is, the outer panoramic image of the outer image-layer-trace (refer 120b of FIG. 16) outside of the base image-layer-trace may be obtained by overlapping the pixels of the frame images having used to reconstruct the base panoramic image by an overlapping amount smaller than the overlapping image of the pixels in reconstructing the base panoramic image or without overlapping the pixels.

Thus, in accordance with the method of obtaining a panoramic image of the third embodiment of this invention, multiple panoramic images such as the panoramic image of inner or outer base image-layer-trace besides the panoramic image of the base image-layer trace may be obtained with one panoramic image scan.

At this time, the image processing unit 400 may reconstruct a panoramic image by connecting frame images selected in the regions of interest after the frame images of all the regions of the base image-layer-trace 120 are obtained. In other words, the panoramic image may be reconstructed by connecting all the obtained frame images, one after another, or by selecting and connecting the frame images of desired regions.

Further, the panoramic image may be reconstructed with the images of some regions. That is, the panoramic image may be reconstructed to the image-layer-trace at the analysis regions to be explained later. In other words, the inner panoramic image of the inner image-layer-trace and the outer panoramic image of the outer image-layer-trace may be reconstructed only with the base image-layer-trace corresponding to the analysis-regions. three regions and at least two analysis regions may determined (S350).

The multiple image-layer-traces may be divided into five (5) regions, and three regions (a first region, a third region and a fifth region) are determined as the analysis regions. At this time, the first region corresponds to left posterior teeth, the third region corresponds to anterior teeth, and the fifth region corresponds to right posterior teeth. A second and a forth regions are non-analysis regions. More detailed explanation can be referred to the FIG. 3.

Next, the multiple image-layer-traces in the same analysis region may be analyzed to select an optimal image-layer-trace most closely related to a focus-trace in each region (S360).

There are various ways of selecting the optimal image-layer-trace of each region. In an embodiment of this invention, the optimal image-layer-trace of each region may be selected with a frequency analysis. More detailed explanation can be referred to the explanations mentioned above referring to FIG. 6.

Next, a connecting-trace linking the optimal image-layer-trace selected in each region is extracted (S370).

In succession, a final-trace is completed by connecting the optimal image-layer-trace selected in each region and the connecting-trace all together (S380). More detailed explanation can be referred to the explanations referring to FIG. 7.

Finally, a panoramic image corresponding to the final-trace is reconstructed (S390).

In other words, a panoramic image is reconstructed in series to the final-trace.

As explained above, in the method and the apparatus for obtaining the panoramic image in accordance with the third embodiment of this invention, the multiple image-layer-traces may be formed by obtaining the inner and outer image-layer-traces with the base image-layer-trace. Further, the panoramic image is reconstructed to the final-trace complete by connecting the optimal image-layer-trace selected in each region and the connecting-trace all together. Thus, it is able to prevent the generation of errors caused by cutting and connecting the images in the conventional art as well as to obtain a clear panoramic image having high image quality.

The method and the apparatus of the third embodiment are identical to those of the first embodiment except the configuration explained above.

This invention may have the excellent effects as the followings.

First, in accordance with the method and the device of this invention for obtaining the panoramic image, it is possible to complete the optimal image-layer-trace to be reconstructed.

Further, in accordance with the method and the device of this invention for obtaining the panoramic image, it is possible to obtain a clear panoramic image which vividly shows an arch of a patient by performing the reconstruct to the optimal image-layer-trace most closely related to a focus-trace.

Also, in accordance with the method and the device of this invention for obtaining the panoramic image, it is also possible to obtain a clear panoramic image by preventing the generation of errors in connection parts even tough using multiple image-layer-traces and composing an optimal image-layer-trace regardless of skill of operators.

The invention claimed is:

1. A method of obtaining a panoramic image, comprising steps of:
    a) positioning an object between an X-ray source exposing X-rays to a base image-layer-trace were regions of interest to be taken in the object and an image sensor receiving the X-rays having penetrated the base image-layer-trace;
    b) obtaining a frame image of a first region of the base image-layer-trace by exposing the X-rays to the first region, a start portion of the base image-layer-trace;
    c) obtaining frame images from a second region adjacent to the first region of the base huge-layer-trace to an $n^{th}$ region, an end portion of the base image-layer-trace, as the X-ray source and the image sensor move, wherein the frame images from the second region to the $n^{th}$ region are obtained by overlapping X-rays penetrating each region of the base image-layer-trace with the X-rays having penetrated previous region of the base image-layer-trace;
    c) obtaining panoramic images correspond to multiple image-layer-traces with use of the frame image of each region of the base image-layer-trace;
    d) dividing the multiple image-layer-traces into at least three regions respectively and determining at least two analysis regions;
    e) selecting an optimal image-layer-trace closely related to a focus-trace by analyzing the multiple image-layer-traces in the same analysis region;
    f) extracting a connecting-trace linking the optimal image-layer-traces selected in the regions;
    g) completing a final-trace by connecting the optimal image-layer-trace selected in each analysis region and the connecting-trace all together; and
    h) reconstructing a panoramic image corresponding to the final-trace.

2. The method of claim 1, wherein the obtaining panoramic images correspond to multiple image-layer-traces at the step d) includes reconstructing base panoramic image with the frame of each region of the base image-layer-trace, reconstructing an inner panoramic image of an inner image-layer-trace by overlapping pixels of the frame images having used to reconstruct the base panoramic image by an overlapping amount larger than an overlapping image of the pixels in reconstructing the base panoramic image, and reconstructing an outer panoramic image of an outer image-layer-trace by overlapping the pixels of the frame images having used to reconstruct the base panoramic image by an overlapping amount smaller than the over lapping image of the pixels in reconstructing the base panoramic image or without overlapping the pixels.

3. The method of claim 2, wherein the inner panoramic image of the inner image-layer-trace and the outer panoramic image of the outer image-layer-trace are reconstructed only with the image-layer-traces in the analysis regions.

4. The method of claim 2, wherein the multiple image-layer-traces are divided into five (5) regions at the step e), and the analysis region is determined with a first region corresponding to left posterior teeth, a third region corresponding to anterior teeth and a fifth region corresponding to right posterior teeth.

5. The method of claim 1, wherein the region of interest is an arch of a patent.

6. The method of claim 1, wherein, at the step c), the optimal image-layer-trace is selected in each region by using a frequency analysis.

7. The method of claim 1, wherein the respective images obtained by overlapping the pixels of the frame images used to forming the panoramic image at step d) are the images obtained by varying shooting angles to the same region of the image-layer-trace.

8. An apparatus for obtaining a panoramic image, comprising:
    an X-ray source exposing X-rays to multiple image-layer-traces where regions of interest of an object exit;
    an image sensor receiving the X-rays having penetrated the multiple image-layer-traces and obtaining images of the image-layer-traces; and
    an image processing device receiving the image obtained by the image sensor and reconstructing panoramic images of the image-layer-traces, wherein the image processing device includes:
        a region determining unit for dividing the multiple image-layer-traces into at least three regions and determining at least two analysis regions;
        a trace selecting unit for analyzing the multiple image-layer-traces in the analysis regions to select an optimal image-layer-trace closely related to a focus-trace in each region;

a connecting-trace extracting unit for extracting a connecting-trace linking the optimal image-layer-traces selected in the regions;

a final-trace completing unit for complaining a final-trace by connecting the optimal image-layer-trace selected in each region and the connecting-trace all together; and an image reconstructing unit for reconstructing a panoramic image corresponding to the final-trace.

9. The apparatus of claim 8, wherein the trace selecting unit selects the optimal image-layer-trace of each region with a frequency analysis.

10. The apparatus of claim 8, wherein the connecting-trace extracting unit extracts the connecting-trace by finding a logarithmic function consistent with a trace linking the optimal image-layer-traces selected in the regions.

11. An apparatus for obtaining a panoramic image, comprising:

an X-ray source exposing X-rays to a base image-layer-trace where regions of interest of an object exit;

a controlling module for exposing the X-rays to all regions of the base image-layer-trace and controlling exposure of the X-rays to overlap the X-rays penetrating each region of the base image-layer-trace with the X-rays having penetrated previous region of the base image-layer-trace; and an image processing device receiving the image obtained by the image sensor and reconstructing a panoramic image of the image-layer-trace, wherein the image processing device includes:

a first image reconstructing unit reconstructing panoramic image layers of multiple image-layer-traces by reconstructing a base panoramic image with the frame of each region of the base image-layer-trace, reconstructing an inner panoramic image of an inner image-layer-trace by overlapping pixels of the frame images having used to reconstruct the base panoramic image by an overlapping amount larger than an overlapping image of the pixels in reconstructing the base panoramic image, and reconstructing an outer panoramic image of an outer image-layer-trace by overlapping the pixels of the frame images having used to reconstruct the base panoramic image by an overlapping amount smaller than the overlapping image of the pixels in reconstructing the base panoramic image or without overlapping the pixels;

a region determining unit for dividing the multiple image-layer-traces into at least three regions and determining at least two analysis regions;

a trace selecting unit for analyzing the multiple image-layer-traces in the analysis regions to select an optimal image-layer-trace closely related to a focus-trace in each region;

a connecting-trace extracting unit for extracting a connecting-trace linking the optimal image-layer-traces selected in the regions;

a final-trace completing unit for completing a final-trace by connecting the optimal image-layer-trace selected in each region and the connecting-trace all together; and a second image reconstructing unit for reconstructing a panoramic image corresponding to the final-trace.

12. The apparatus of claim 11, wherein the X-ray source and the image sensor move along a predetermined trace around the object, and the image sensor obtains frame image, as unit images, with the X-rays exposed to each region.

13. The apparatus of claim 11, wherein the first image reconstructing unit reconstructs the inner panoramic image of the inner image-layer-trace and the outer panoramic image of the outer image-layer-trace only with the image-layer-traces in the analysis regions.

14. The apparatus of claim 11, wherein the trace selecting unit selects the optimal image-layer-trace of each region with a frequency analysis.

15. The apparatus of claim 11, wherein the connecting-trace extracting unit extracts the connecting-trace by finding a logarithmic function consistent with a trace linking the optimal image-layer-traces selected in the regions.

* * * * *